United States Patent [19]
Sekel

[11] Patent Number: 5,580,352
[45] Date of Patent: Dec. 3, 1996

[54] DISTAL SHAFT WITH FAST AND SLOW SCREW THREADS

[76] Inventor: Ronald Sekel, 42 Montgomery Street, Kogarah, NSW 2217, Australia

[21] Appl. No.: 952,515

[22] PCT Filed: Jun. 6, 1991

[86] PCT No.: PCT/AU91/00244

§ 371 Date: Feb. 1, 1993

§ 102(e) Date: Feb. 1, 1993

[87] PCT Pub. No.: WO91/18559

PCT Pub. Date: Dec. 12, 1991

[30] Foreign Application Priority Data

Jun. 6, 1990 [AU] Australia ................... PK0508

[51] Int. Cl.⁶ ............... A61F 2/32; A61F 5/00
[52] U.S. Cl. ............... 623/23; 623/18; 606/62
[58] Field of Search ............... 623/16, 18, 19, 623/22, 23; 606/72, 73

[56] References Cited

U.S. PATENT DOCUMENTS

| | | | |
|---|---|---|---|
| 4,175,555 | 11/1979 | Herbert | 606/73 |
| 4,463,753 | 8/1984 | Gustilo | 606/73 |
| 4,822,370 | 4/1989 | Schelhas | 623/23 |
| 4,851,007 | 7/1989 | Gray | 623/23 |
| 4,878,916 | 11/1989 | Rhenter et al. | 623/22 |
| 5,019,079 | 5/1991 | Ross | 606/72 |
| 5,259,398 | 11/1993 | Vrespa | 606/73 |

FOREIGN PATENT DOCUMENTS

| | | | |
|---|---|---|---|
| 0038897 | 11/1981 | European Pat. Off. | 623/23 |
| 0201407 | 11/1986 | European Pat. Off. | 623/23 |
| 2600526 | 12/1987 | France | 623/22 |
| 2622791 | 5/1989 | France | 623/22 |
| 2558446 | 7/1976 | Germany | 623/22 |

*Primary Examiner*—David Isabella
*Attorney, Agent, or Firm*—McAulay Fisher Nissen Goldberg & Kiel, LLP

[57] ABSTRACT

A femoral prosthesis adapted for insertion into the medullary cavity of a femur. The prosthesis including a distal shaft, a neck portion detachable from the distal shaft and a joint head detachable from the neck portion. The distal shaft having two spaced tapered threaded portion thereabout with differing pitch to prevent undesired counter rotation of the prosthesis thereby preventing axial withdrawal of the distal shaft from the femur.

10 Claims, 5 Drawing Sheets

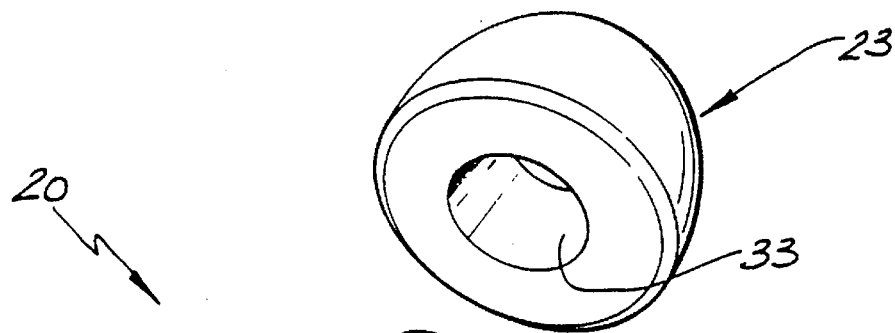
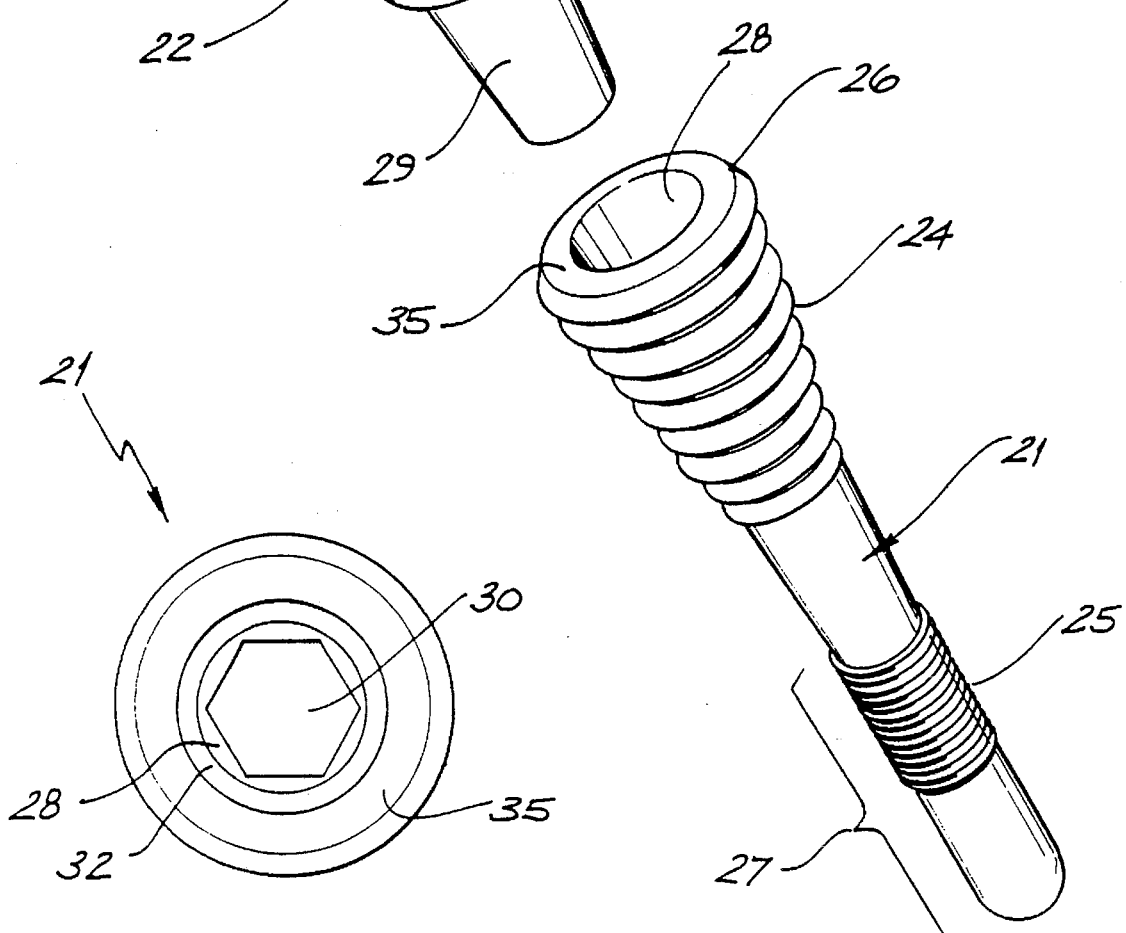
FIG. 6
FIG. 7

DISTAL SHAFT WITH FAST AND SLOW SCREW THREADS

The present invention relates to surgical prostheses and more particularly, relates to a femoral component for use in hip replacements either at first instance or in revision hip operations following an earlier implant failure.

Hip replacements are a common orthopaedic surgical procedure and are usually necessitated by degenerative disease of the hip joint, hip trauma or disease of the hip creating later hip trauma.

In a total hip replacement, the surgical procedure may involve reaming of the acetabulum, reaming of the proximal medullary cavity of the femur and inserting a prosthesis into the said medullary cavity to replace the natural femoral head.

The head of the prosthesis (usually formed by a detachable ceramic ball) mates with the acetabulum in the same manner that the natural femoral head mates with the acetabulum in a normal hip joint.

Depending upon the dictates of the pathology of the joint not all hip replacements require reaming of the acetabulum. In some cases only the femoral head requires replacement; for example, in a fractured neck of femur. The invention may be used in hemiarthroplasty or as the femoral component of a total hip arthroplasty.

There are in existence a number of hip prostheses which have been used to replace the femoral head. Whilst each of the prior art femoral head prostheses have enjoyed widespread use with varying degrees of success, each have suffered from certain attendant disadvantages.

One generally known and widely used prosthesis typically comprises an arcuate distal shaft having a gradual taper along its full length and terminating proximally in a neck which mates with the head of the prosthesis via a Morse taper. The shaft is inserted into the indra medullary cavity of the femur.

This prosthesis is fitted after the surgeon has reamed out the medullary cavity to an extent conducive to the production of tight interfitting between bone and prosthesis when the prosthesis is hammered into position. In practice, the reaming followed by sizing with the prosthesis may be carried out a number of times i.e., reaming followed by inserting the prosthesis until there is a small distance of travel of the shaft left near the neck of the femur to enable final hammering into position to thereby create tight interfitting between prosthesis and bone. In the final stages of this procedure, when the prosthesis is hammered home, care must be taken by the surgeon to avoid exploding the femur by creating hoop stresses beyond the modulus of elasticity of the bone. The tolerable limits of bone elasticity are guaged mainly by the experience of and feel by the surgeon.

Femoral explosion is one major drawback when using this prior art prosthesis both during insertion and extraction, however, explosion during insertion is largely due to poor surgical technique.

In the past, cementing of the prosthesis has also been employed, however, problems have existed with the use of cement. Failures in hip prostheses have occurred due to loosening at the cement bone interface and at the prosthesis bone interface. In some patients, a rotational failure of the prosthesis can be generated when a patient moves from a seating to a standing position.

Also, artificial hips may loosen and fail due to repetitive movement of the distal shaft induced by the locomotion of a wearer. This may eventually lead to a prosthesis failure and possibly unwanted axial dislocation; for example subsidence of the prosthesis.

One feature of the existing prostheses is a series of indentations which have been moulded into the distal shaft in order to encourage and stimulate bone growth therein. This bone ingrowth assists in holding the prosthesis firmly in position and also provides a keying and locking effect thereby lessening the possibility of rotational failure and/or unwanted axial subsidence of the prosthesis.

A further problem which exists with this type of prior art prosthesis and in particular with the distal shaft design is the difficulty in removal from the medullary cavity of a failed prosthesis. The procedure to replace a failed prosthesis, known as a revision hip replacement, necessitates full extraction of the failed prosthesis from the medullary cavity. Where the prosthesis has been held in position by bone growth into the aforesaid recesses of the distal shaft, extraction of the prosthesis can sometimes be extremely difficult, and in some unfortunate instances, may necessitate total longitudinal division of the femur into at least two pieces. Even after division of the femur in this way, a particularly recalcitrant prosthesis firmly affixed to one half of the bone may, in order to effect removal thereof, necessitate further undesirable femoral destruction. After removal of the failed prosthesis by femoral destruction, the divided femoral bones must then be rewired and/or screwed. A new prosthesis can be inserted either before the bones are rewired or after rewiring in accordance with normal procedure.

Clearly this surgical problem is wholly undesirable and results in increased theatre time and an increased period of convalesence for a patient as the divided bone requires additional time to heal.

Whilst prostheses of this type have been in use for some time and have met with considerable field success, the attendant disadvantages of the device are so significant that improvements are necessitated.

Other prosthesis designs are also used having screw threads on the distal shaft however, these suffer from the major disadvantage that it is very difficult for the surgeon to achieve, co-incidence between the correct orientation of the prosthesis at full screw tightness and proper alignment or anteversion between the prosthesis head and the acetabulum. This requires considerable skill on the part of the surgeon with very little margin for error due to the critical alignment and screw tightness requirements. For this reason surgeons have not utilised the screw prostheses as much as the previously described prosthesis. A further disadvantage of the existing screw prosthesis is its poor resistance to rotational effects which can result in unwanted reverse rotational withdrawal from the femoral medullary cavity. This in turn upsets the critical anteversion between femoral head and acetabulum thereby often resulting in the need for a revision hip operation. The withdrawal by unscrewing of this prosthesis does nevertheless have an advantage in revision hip operations where the existing prosthesis is to be withdrawn and removed by the surgeon however, the problem of unwanted reverse rotation of an in situ screw prosthesis is too great in proportion to the advantage provided by the single screw thread. Prior art prostheses employing single screw threads have thus been quite unsatisfactory resulting in their limited use.

The present invention seeks to ameliorate or eliminate the attendant disadvantages which have been manifest in use of the prior art hip prostheses by providing an improved prosthesis.

In addition to providing significant advantages over the prior art, the present invention overcomes the problems associated with, unwanted withdrawal of screw thread prostheses, obtaining of correct anteversion of screw thread prostheses with the acetabulum at full screw tightness, and problem extractions of prostheses during revision hips.

The invention combines the benefits of the known prior art prostheses, provides further benefits and eliminates the prior art disadvantages.

In its broadest form the present invention comprises; a femoral prosthesis of the type comprising a distal shaft neck and head and adapted for insertion into the medullary cavity of the femur to thereby form a replacement for the natural femoral head; characterised in that the femoral prosthesis comprises;

a first threaded portion and a second threaded portion on said distal shaft with a cavity at one end of said distal shaft, a detachable member adapted to mate at one of its ends with the said cavity and adapted at its other end to mate with an artificial head, whereupon when said distal shaft is inserted into and fixed in situ the medullary cavity of the femur correct anteversion between said head and the acetabulum of a patent is effected by relative rotational movement between said detachable member and said distal shaft.

In another broad form the present invention comprises; a femoral prosthesis of the type adapted for insertion into the medullary cavity of the femur to thereby form a replacement for the femoral head characterised in that the femoral prosthesis comprises;

a distal shaft having at least one threaded portion thereon and a cavity at one end, a member configured to interfit via one end within said cavity and via the other end to interfit with an artificial head wherein when said distal shaft, said member and said artificial head are mated together, an artificial hip is thereby formed.

In another form the invention comprises a femoral prosthesis of the type adapted for insertion into the medullary cavity of the femur to thereby form a replacement for the femoral head or hip; characterised in that the femoral prosthesis comprises a distal shaft having at least two different pitch screw threads thereabout, said distal shaft terminating at one end in a neck portion configured to receive an elbow member to thereby form in conjunction with a head portion an artificial hip.

In its broadest form the present invention comprises a femoral prosthesis comprising a threaded distal shaft, a detachable elbow having a double Morse taper and a head.

In one broad form the present invention comprises:

a femoral prosthesis adapted for insertion into the modullary cavity of a femur said prosthesis comprising, a distal shaft, a neck portion detachable from said distal shaft and a head detachable from said neck portion characterised in that the neck portion comprises an elbow having means at either end to enable male female or female male mating with said distal shaft and also with said head to create tight interfitting therebetween, said elbow being rotatable relative to said shaft and head prior to effecting said tight interfitting and while said distal shaft is fixed in situ.

In another broad form the invention comprises:

A femoral prosthesis adapted for insertion into the medullary cavity of a femur said prosthesis comprising a distal shaft, a neck and a head; characterised in that the distal shaft comprises first and second spaced apart threaded regions thereon.

In an alternative form the present invention comprises:

A distal shaft for use in a femoral prosthesis said shaft having a recess at the proximal end adapted to receive a tapered portion on an elbow said shaft also comprising spaced apart threaded portions.

In a further form the invention comprises:

An elbow for use in a femoral prosthesis said elbow comprising two legs disposed at an obtuse angle to each other, each of said legs terminating at its extremity in a tapered portion.

In one preferred embodiment the invention comprises a tapered distal shaft having two spaced apart tapered threaded portions thereabout with differing pitch and a female tapered cavity at one end adapted to detachably receive a first male part of a corresponding mating member in a tight interfitting relationship, with the mating member also having a second male part adapted to tightly interfit with a female cavity in a head member.

Preferably the interfitting between the first and second male parts and the corresponding female parts is effected by a Morse taper at either end of the mating member, thereby creating a double MORSE taper, allowing interengagement between the distal shaft and the mating member and between the mating member and an acetabular cup.

Although the prosthesis is ideally intended to be formed by detachable communication between the distal shaft and an elbow having means thereon which forms double MORSE taper connections, the prosthesis may be fabricated in one piece with two threads on the distal shaft with the shaft terminating in a single Morse taper which engages the head member.

The present invention will now be described in more detail according to a preferred but non limiting embodiment and with reference to the accompanying illustrations wherein;

FIG. 6 shows an exploded view of a prosthesis according to a preferred embodiment.

FIG. 7 shows a plan view of the distal shaft of FIG. 6.

Figures 1, 2, 3:
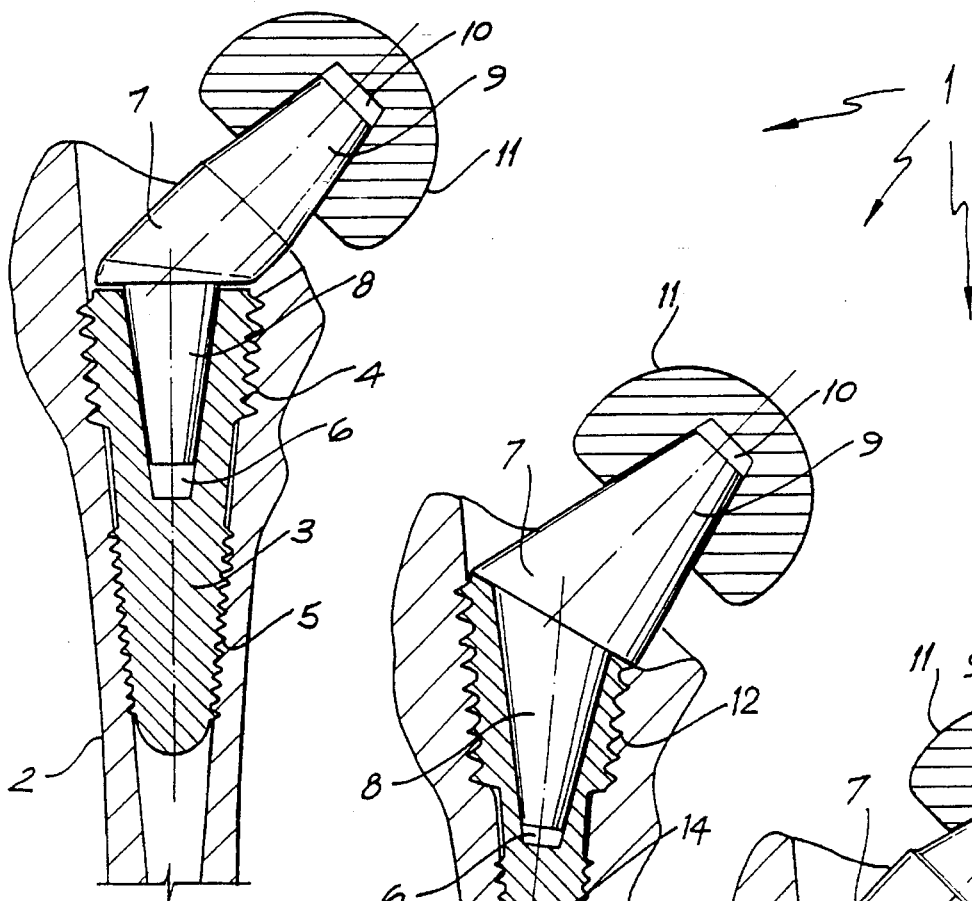
FIG. 1 shows a long sectional view of the proximal portion of a femur with an assembled prosthesis of the present invention inserted therein according to a preferred embodiment.
FIG. 2 shows a long sectional view of the upper portion of a femur with a prosthesis according to an alternative embodiment inserted therein.
FIGS. 3, 4 and 5 show various embodiments of the prosthesis of the present invention.

Referring to FIG. 1 there is shown a prosthesis 1 located proximally in femoral long section 2.

The prosthesis according to the embodiment of FIG. 1 essentially comprises a distal shaft 3 having two spaced apart threads 4 and 5 disposed helically and peripherally about the longitudinal axis of the shaft. The distal shaft 3 has a reducing taper with the thread 4 thereabout having a fast helix and the thread 5 having a slow helix effected by differing thread pitch.

At the upper end of the distal shaft there exists a tapered recess 6. The recess 6 is adapted to receive an elbow or neck 7 which has a tapered male profile part 8 which taper is the reverse that of recess 6 to facilitate upon coupling a tight male/female interfitting therebetween. This type of connection is known as a Morse taper not hitherto previously known in this specific application.

The elbow 7 also comprises a tapered end forming a male profile part 9 which is adapted to mate with female recess 10 in head 11, thus forming a second Morse taper according to conventional usage.

In order to insert the prosthesis, the surgeon reams out the medullary cavity of the femur to enable mutual comparability between the bone and prosthesis. The reaming which takes place is commensurate with required thread depth and distal shaft width and taper. The bone cross section is reamed to approximately the width and length of the taper over the thread length less the thread depth. Thus the reaming for slow thread 5 will be considerably less than that for fast thread 4. The threading may be done preferably with a truncated cone threader similar to that shown in FIG. 10. The shaft 3 is screwed into the medullary cavity and if necessary, with bone graft supplementation to ensure a strong prosthesis-bone bond. One major advantage of this prosthesis is the optional elimination of the need for cementing or precoating of the prosthesis. Although the prosthesis may be pre-coated with hydroxyapetite to stimulate bone ingrowth, this is not essential.

Figure 10:
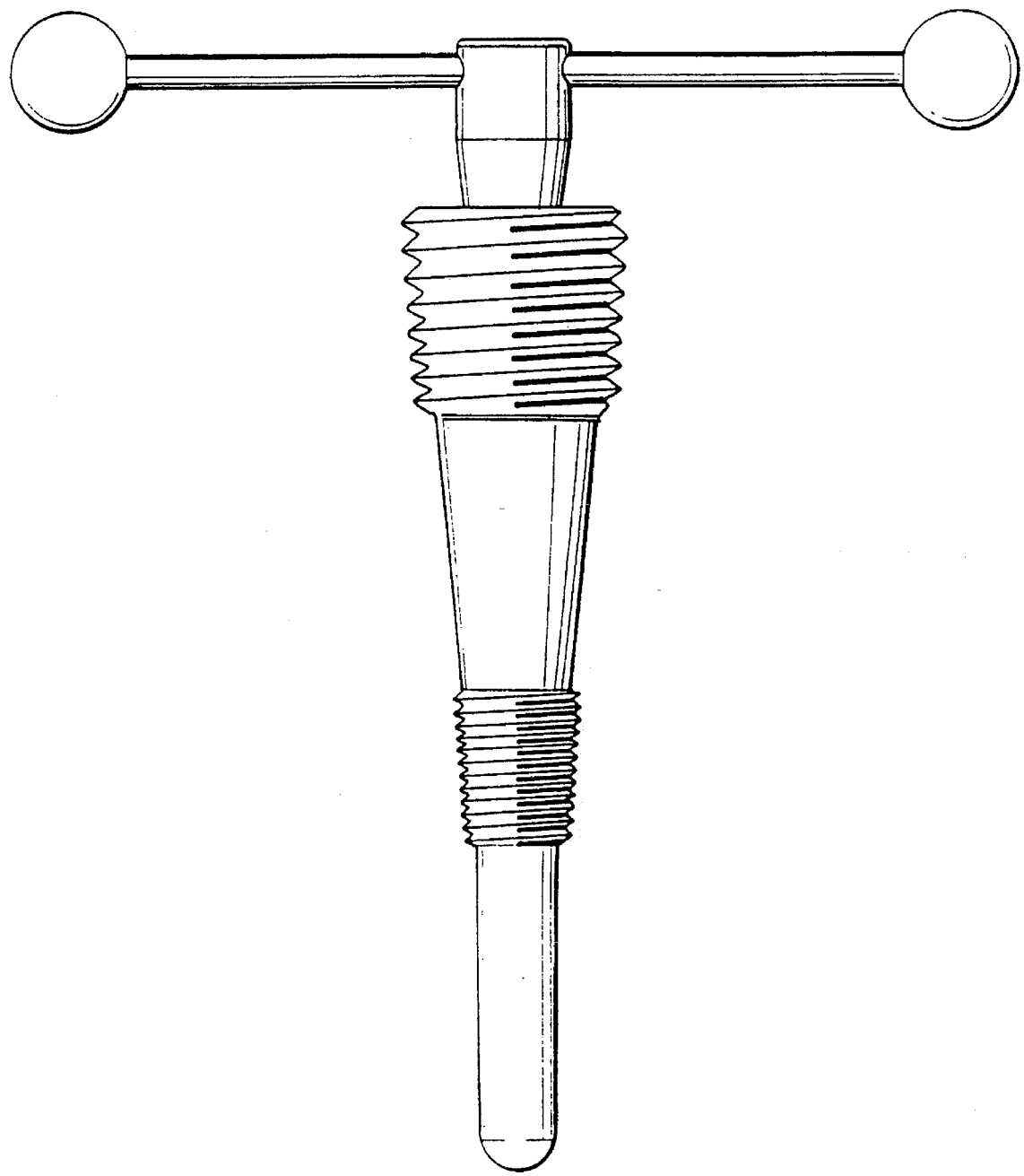
FIG. 10 shows a tool which may typically be used in preparation of the medullary cavity to receive the prosthesis.

In practice, the distal shaft 3 is screwed into position following reaming using the truncated conical tool of FIG. 10 or an allen key with the assistance of a torque wrench. Once the distal shaft is in position, the elbow 7 may be inserted into cavity 6 and rotated by the surgeon to the correct position of alignment with the acetabulum (not shown). Once this position is determined, the elbow is hammered to effect the tight interfit with the distal shaft. The Morse taper prevents unwanted rotational and axial movement, once the elbow is aligned and driven home. Finally, the head 11 (a conventional ceramic, chrome cobalt, plastic or titanium cup) is hammered onto male profile part 10 of elbow 7 to complete the location of the prosthesis. The use of the double Morse tapered elbow allows rotational alignment of the head relative to the acetabulum or an acetabular cup after screwing in of the distal shaft 3 is complete, thereby enabling a convenient final fine adjustment of the prosthesis. The double threads on the distal shaft 3 create a compression force in the bone thereby removing the problem which existed in prior art 'screw in' prostheses of unwanted counter rotation leading to axial withdrawal of the distal shaft.

The use of the double Morse taper therefore allows the surgeon to conveniently achieve accurate anteversion of the femoral head and neck at the appropriate angle.

FIG. 2 shows an alternative embodiment of the prosthesis of FIG. 1, this time with a first wide threaded portion 12 and a narrower threaded portion 13. Fast thread 12 and thread 13 combine to create a compressive force to hold the distal shaft 14 firmly within the medullary cavity. This prosthesis may be implanted after medullary cavity preparation using the tool of FIG. 10 to prepare the thread paths.

Figures 4, 5:
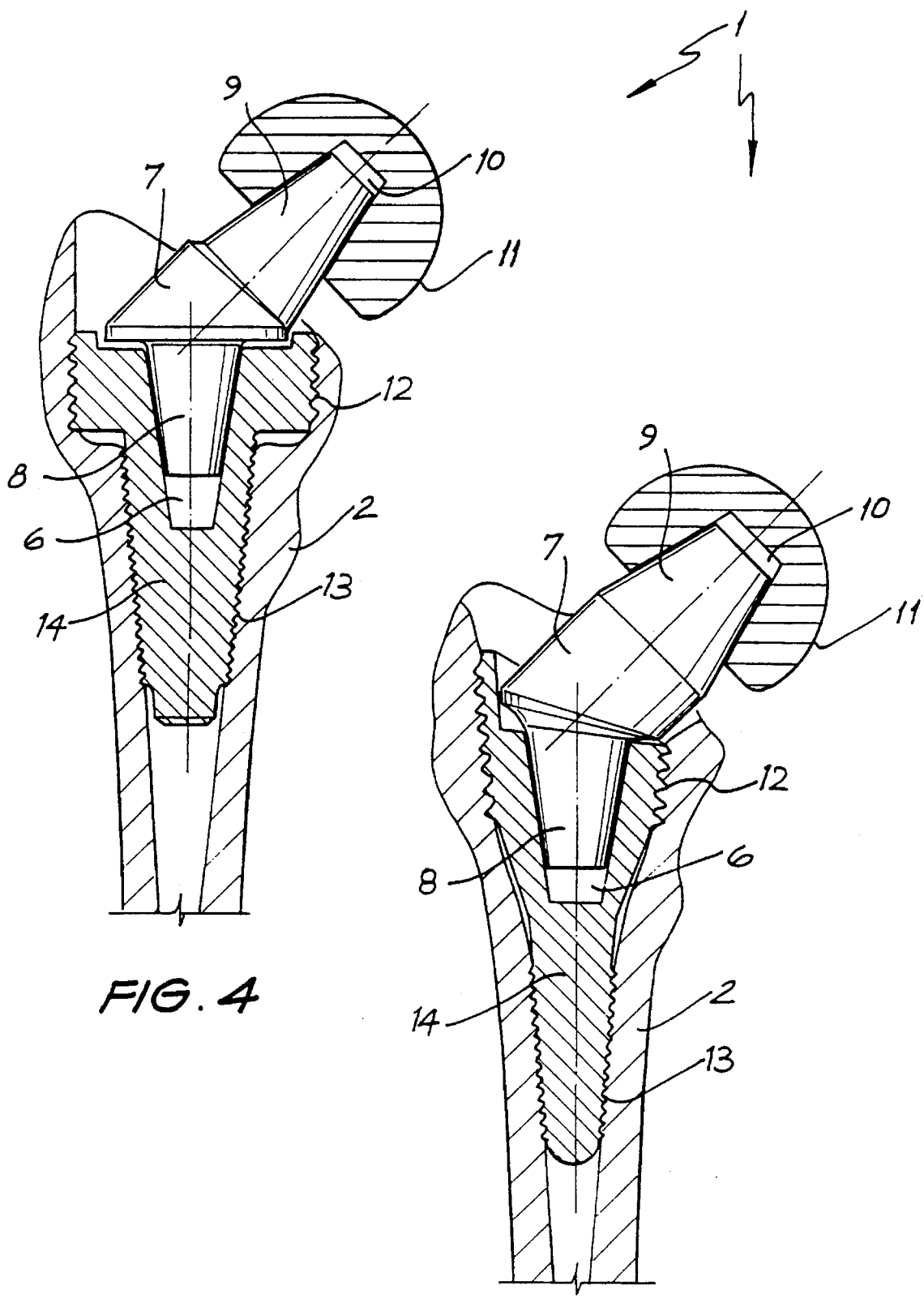

FIGS. 3, 4 and 5 show further alternative embodiments of the present invention. The threads thereon could be scinted, beaded or precoated.

Referring to FIG. 6 there is shown an exploded view of a femoral prosthesis 20 according a preferred embodiment of the invention. The prosthesis 20 comprises a distal shaft 21, a detachable neck comprising an elbow 22 and a head 23. The distal shaft 21 also comprises threaded portions 24 and 25 with threaded portion 24 being at or near the proximal end 26 of the distal shaft 21 and with the threaded portion 25 being spaced apart distally at location 27. When the distal shaft is screwed into position as previously described the threaded portions 24 and 25 due to their respective helix configurations cause a compressive force to be exerted on the wall of the medullary cavity of the bone. This results in a strong implant with high rotational stability and high resistance to unwanted axial withdrawal due to rotational failure. Referring to FIG. 7 distal shaft 21 has a female recess 28 at the proximal end 26 for coupling with tapered male profile part 29 of elbow 22. Distal shaft 21 also comprises a hexagonal profile 30 adapted to receive an allen key for unscrewing of the distal shaft when removal of same is required. Elbow 22 comprises tapered portions 29 and 31 which together form the neck of the prosthesis. Preferably tapered portion 29 is longer than tapered end 31 in view of the fact that the depth of penetration of tapered portion 29 is necessarily greater than that required for taper 31. In use after the distal shaft 21 is secured in position by the surgeon, the elbow 22 is gently dropped into recess 28 whilst maintaining a sufficient degree of loseness for rotation of the elbow 22 relative to the distal shaft 21. When the correct anteversion is determined by the surgeon, the elbow 22 is driven home to a condition of tight interfitting between taper 29 and the wall 32 of recess 28. Taper 31 engages recess 33 of the head 23 to complete the femoral prosthesis assembly.

Elbow 22 is also adapted with a collar or flange 34 which provides a levering point to enable the surgeon to remove the elbow where the femoral prosthesis is to be removed from a patient. The surgeon may lever against the upper crest 35 of the distal shaft 21 and against the collar or flange 34 in order to break the tight interfitting. Collar 34 as shown is merely one embodiment for facilitating separation between elbow 22 and distal shaft 21. It will be recognised that other means can be adapted to the elbow 22 in order to facilitate separation prior to removal of the distal shaft.

Figure 8:
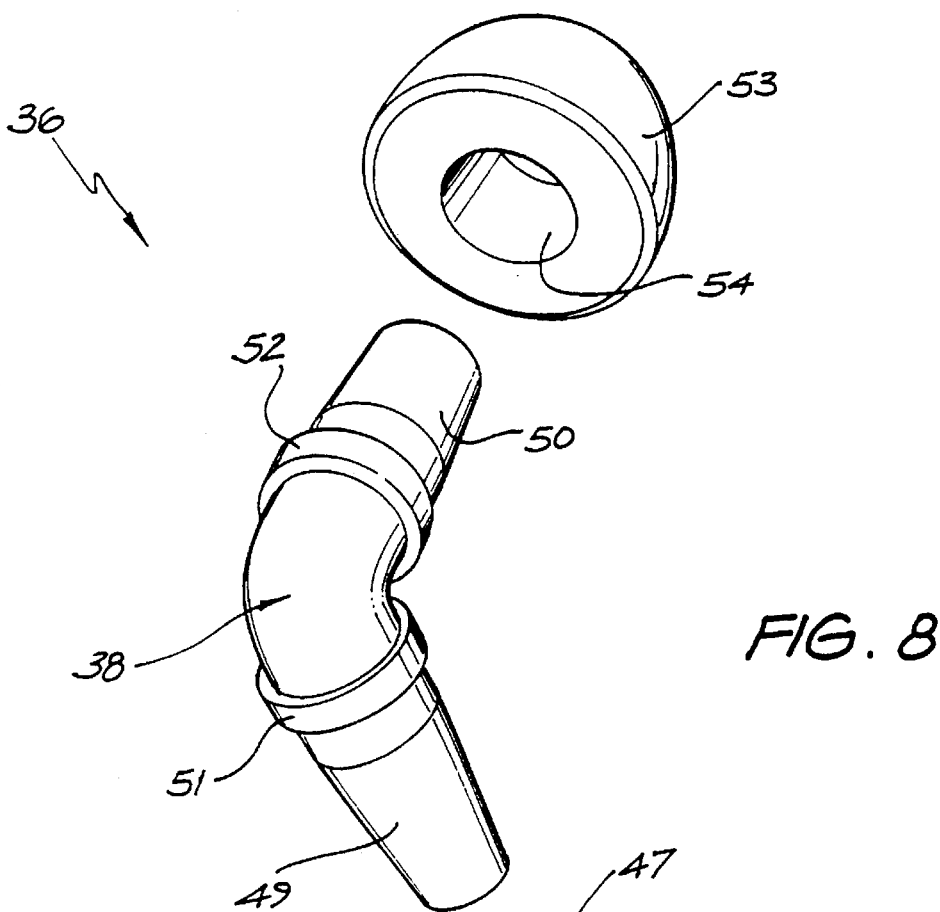
FIG. 8 shows an exploded view of a prosthesis according to a preferred embodiment of the invention.

Referring to FIG. 8 there is shown an exploded view of a hip prosthesis 36 with more specific design geometry for the distal shaft 37 and the neck or elbow 38.

Figure 9:
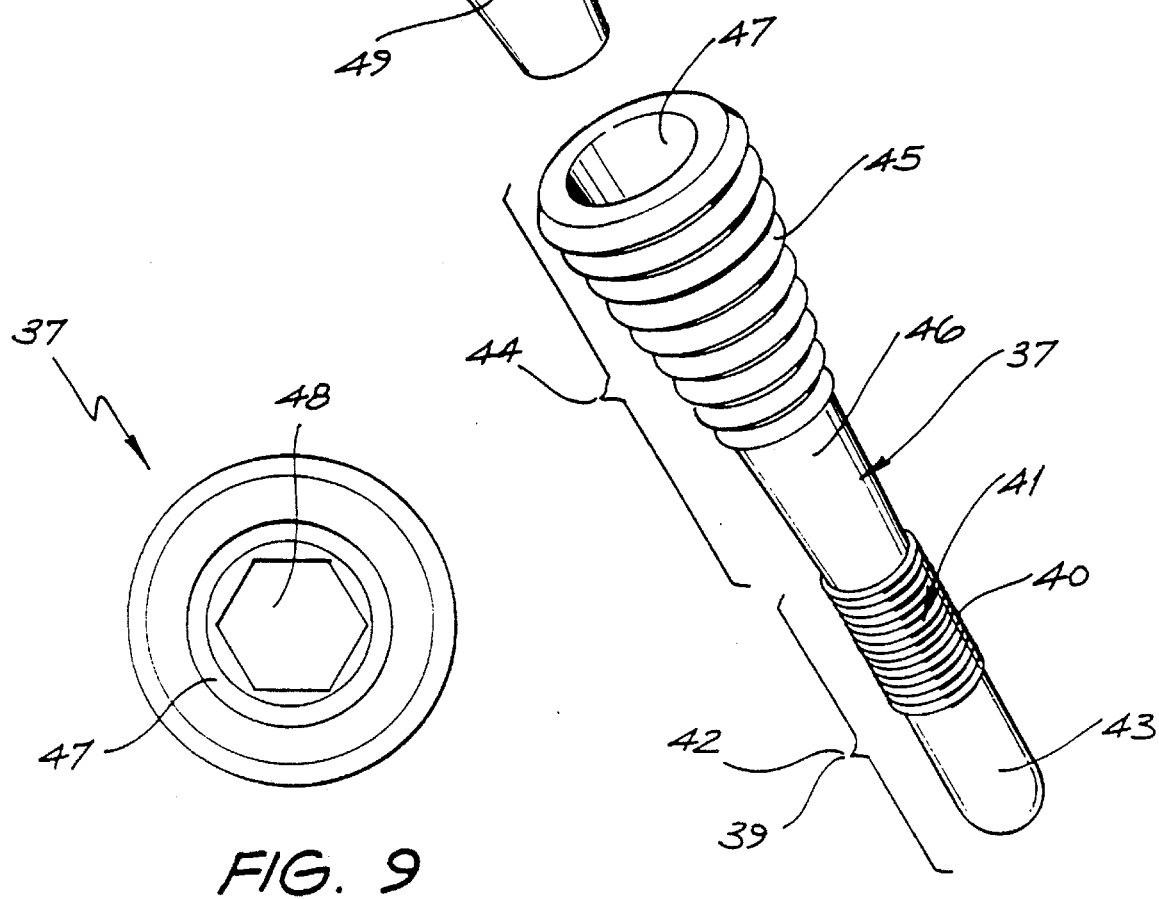
FIG. 9 shows a plan view of the distal shaft of FIG. 8.

FIG. 9 shows a plan view of the distal shaft 37. At the distal end 39 of the shaft 37 is a screw thread 40 about a region 41 of constant width. The diameters of the distal shaft core 42 fall preferably within the range of 9 mm to 13 mm. The distal core 42 comprises the thread 40 and non threaded region 43. Thread 40 is configured as a slow thread. Preferably the lengths of thread 40 and non threaded region 43 would be 35 mm and 22 mm respectively.

At the proximal region 44 of the distal shaft 37 is a tapered screw thread 45 and a non threaded tapered region 46 with the thread 45 approximately 40 mm in length and the region 46 approximating 33 mm in length. Thread 45 is configured as a fast helix relative to the helix of thread 40. The proximal region 44 preferably has a 10 degree taper in order to approximate anatomical characteristics of the proximal medullary cavity of a femur. Preferably proximal core diameters are within the region 20 mm to 26 mm with the outside diameter including the thread being an additional 1 to 2.5 mm. Proximal region 44 of the shaft 37 is adapted with a Morse one taper 47. Ideally a taper within the Morse range of ¾ to 1.5 is preferred however, this is not to be construed as a limiting parameter. The Morse taper 47 terminates in hexagonal recess 48 which provides means for insertion and deliberate withdrawal of the shaft 37 for instance, in the event of a revision hip operation.

Preferably, the distal shaft is made from Titanium or chrome-cobalt alloy with an hydroxyapetite coating being applied to the threaded regions to stimulate osteogenesis or bone ingrowth around the shaft 37. Alternatively chrome cobalt with beading to stimulate bone ingrowth may be used.

In the prior art prosthesis distal shafts have relied upon boney ingrowth and/or circumferential point fixation in order to provide proper anchorage. Distal shafts which have been configured anatomically have often failed due to a lack of reliance on point fixation generating hoop stresses. Many of the prior art prostheses have been generally square or rectangular which has meant that due to the shape of the intramedullary cavity there is limited contact between prosthesis and bone hence localised force distribution.

The distal shaft 37 of the present invention increases the prosthesis bone contact area having a resultant more even contact force distribution. Prosthesis 36 also comprises elbow or neck 38 which is configured at an obtuse angle between 90° and 180°. Elbow 38 comprises a first Morse taper 49 and a second larger Morse taper 50. The difference in the tapers is to prevent an error in mating between the elbow 38 and the distal shaft 37. Taper 49 is preferably a Morse 1 taper with second taper 50 being preferably Morse 1.5.

Elbow 48 is also adapted with collars 51 and 52 to facilitate release of the Morse tapers.

Morse 1 taper 49 engages taper 47 in distal shaft 37. Taper 50 engages head 53 via a female recess 54 therein. Head 53 may generally be 28, 32 or 38 mm in diameter with an internal Morse taper of 1.5. Once the distal shaft is inserted by the surgeon the configuration of the elbow will enable accurate approximation of the distance in the particular patient from the midline of the femur to the correct location of the head 53 in the acetabulum or in the acetabular cup in the case of a total hip replacement. Thus the double Morse taper on the elbow leads the surgeon to the anatomical centre of the previous natural remoral head.

Appropriate anteversion may be achieved by the surgeon with the elbow 48 prior to wedging of taper 49 in the distal shaft taper 47.

If the elbow is to be removed, the Morse taper is easily broken by levering or wedging against collar 51. Similarly where head 53 is to be removed levering or wedging against collar 52 facilitates this.

Reaming of the medullarly cavity prior to fixation of the prosthesis results in distal fixation occurring along a plane normal to the cortex bone when a femur is viewed in long section. Proximal fixation occurs principally in a plane at 90° to that for distal fixation, anteriorly and posteriorly.

With the present invention the surgeon is more able to predict hoop stresses generated in fixation.

The distal shaft 37 may be lengthened where necessary especially where a fresh bone contact area is required if a previously used prosthesis fixation area has been degraded.

Similarly, the elbow may be adapted for lengthening by use of extension pieces so that the exact location of a removed anatomical head may be located.

The prosthesis of the present invention places some reliance on the compressive forces generated by the fast and slow threads along with the frictional resistance generated by bone prosthesis contact to resist axial dislocation of the prosthesis.

In order to guard against the unlikely event of reverse rotation of the prosthesis, a longitudinal channel may be formed along the medullary cavity wall to facilitate keying of the prosthesis to the bone. The key would need a corresponding longitudinal slot in the prosthesis shaft.

It will be recognised by persons skilled in the art that numerous variations and modifications may be made to the invention as broadly described herein without departing from the overall spirit and scope of the invention.

I claim:

1. A distal shaft for use with a hip prosthesis which includes a detachable elbow component and a detachable head component, the shaft being insertable wholly within and in axial alignment with a medullary cavity of a femur, the shaft having a flared proximal end provided with a tapered recess in axial alignment with the shaft for receiving the elbow component and also having a tapered distal end, the shaft being provided with a first helical thread and a second helical thread spaced apart from one another.

2. A distal shaft according to claim 1 wherein the first thread is a wide tapered helical thread located proximately to the flared proximal end of the shaft and the second thread is a narrow helical thread disposed towards the narrow distal end of the shaft.

3. A distal shaft according to claim 2 wherein the threads are equal in length with respect to the shaft.

4. A distal shaft according to claim 2 wherein the threads are different in length with respect to the shaft.

5. A distal shaft according to claim 1 wherein said first and second threads are structured to have different helix configurations such that when said shaft is inserted into the medullary cavity of a femur, said first and second threads induce a compression force into the femur.

6. A distal shaft according to claim 5 wherein the said first thread and said second thread have similar pitches.

7. A distal shaft according to claim 5 wherein the said first thread and said second thread have different pitches.

8. A distal shaft according to claim 5 wherein the elbow component is capable of rotation relative to the shaft prior to effecting tight interfitting with the shaft.

9. A distal shaft according to claim 5 wherein the tapered recess in the shaft is a Morse taper.

10. A distal shaft according to claim 1 wherein the first and the second helical thread are spaced apart from one another by a threadless section of the shaft.

* * * * *